United States Patent [19]

Wolf

[11] 4,150,574

[45] Apr. 24, 1979

[54] FLUID SAMPLING SYSTEM

[76] Inventor: Harry Wolf, 5707 Rhodes Ave., North Hollywood, Calif. 91607

[21] Appl. No.: 865,115

[22] Filed: Dec. 28, 1977

[51] Int. Cl.² .......................... G01N 1/22; G01N 1/26
[52] U.S. Cl. ............................... 73/421.5 R; 73/422 R
[58] Field of Search ...... 73/421 A, 421.5 R, 421.5 A, 73/422 R

[56] References Cited

U.S. PATENT DOCUMENTS

| | | | |
|---|---|---|---|
| 2,475,857 | 7/1949 | Reinert | 73/421.5 R |
| 2,518,574 | 8/1950 | Skopecek | 73/422 R X |
| 3,369,346 | 2/1968 | Wildbolz et al. | 73/421.5 R X |
| 3,461,727 | 8/1969 | Everhard et al. | 73/421.5 R |
| 3,538,748 | 11/1970 | Linsell et al. | 73/422 R X |
| 3,587,323 | 6/1971 | Benjaminson et al. | 73/421.5 R |
| 3,765,226 | 10/1973 | Strickland et al. | 73/422 R X |
| 3,803,921 | 4/1974 | Dieterich | 73/422 R |
| 3,965,749 | 6/1976 | Hadden et al. | 73/421.5 R |
| 4,047,437 | 9/1977 | Brooks | 73/421.5 A |

*Primary Examiner*—Charles Gorenstein
*Attorney, Agent, or Firm*—Lewis B. Sternfels

[57] ABSTRACT

Fluid, such as air, flowing through a duct is sampled by a detector in a chamber by withdrawing a portion of the fluid from the duct by an impact tube which connects the duct to an inlet in the sampling chamber. Several openings in the impact tube extend across the duct and face into the direction of fluid flow in order to obtain a cross-sectional and representative sample of the fluid. To insure that an adequate sample is obtained, one or more venturi tubes are also placed into the direction of the flow path of the fluid and these venturi tubes are connected to the outlet of the sampling chamber to exert a pressure in the chamber which is negative with respect to the chamber inlet from the impact tube.

5 Claims, 5 Drawing Figures

FLUID SAMPLING SYSTEM

BACKGROUND OF THE INVENTION

1. Field of the Invention

The present invention relates to means by which fluid from a path of its flow may be sampled.

2. Description of the Prior Art

Fluid sampling systems are used for detection of products of combustion and of the chemical nature of gases and fluids, such as existing in smoke stacks, mines, air conditioning ducts, etc. With respect to air conditioning ducts, it is conventional to place a pair of tubes across the duct. Holes in one tube face into the direction of air flow while holes in the other tube are at right angles to the direction of air flow. Thus, air enters the first holes, passes to the detector and exhausts through those holes which are perpendicular to the direction of air flow. In a second air conditioning system, the end of the inlet tube is cut at an angle facing the direction of air flow so that air may pass into the tube while the exit tube is cut away from the direction of air flow.

In both cases, only a very small pressure differential is created which is so small that minimum air flow of 500 feet per minute is required to insure an adequate sample. In general, sampling in conventional systems is taken utilizing air flows between 500 feet per minute and 3,000 feet per minute velocity. At these velocities, the pressure differential extends from 0.015 inches of water to 0.56 inches of water. Such small sampling may be insufficient in terms of fire protection, that is, the presence of a fire is not detected until the fire has substantially advanced beyond its initial stages. At that point, serious property damage and threat to life may result.

Similar detection systems are also required for toxic materials or other dangerous gases.

SUMMARY OF THE INVENTION

The present invention overcomes these and other problems by providing a fluid sampling system in which a sample of a fluid flowing in a path is conducted to a detector not only by the force of fluid being directed into the detector but also by creating a fluid pressure in the detector which is negative with respect to the detector's inlet. The preferred means by which a negative fluid pressure is created is by use of a venturi tube placed also in the path of the fluid flow. Samples from an air duct have been measured at approximately four times greater than that of prior art systems.

It is, therefore, an object of the present invention to provide for sampling of fluids taken from a flow of the fluids.

Another object is to provide for increased sampling of such fluids.

Another object is to provide for such sampling at flow velocities less than conventionally used.

Anoter object is to provide for a means of such increased sampling by use of non-moveable parts.

Other aims and objects as well as a more complete understanding of the present invention will appear from the following explanation of an exemplary embodiment and the accompanying drawings thereof.

DESCRIPTION OF THE PREFERRED EMBODIMENT

Figure 1:
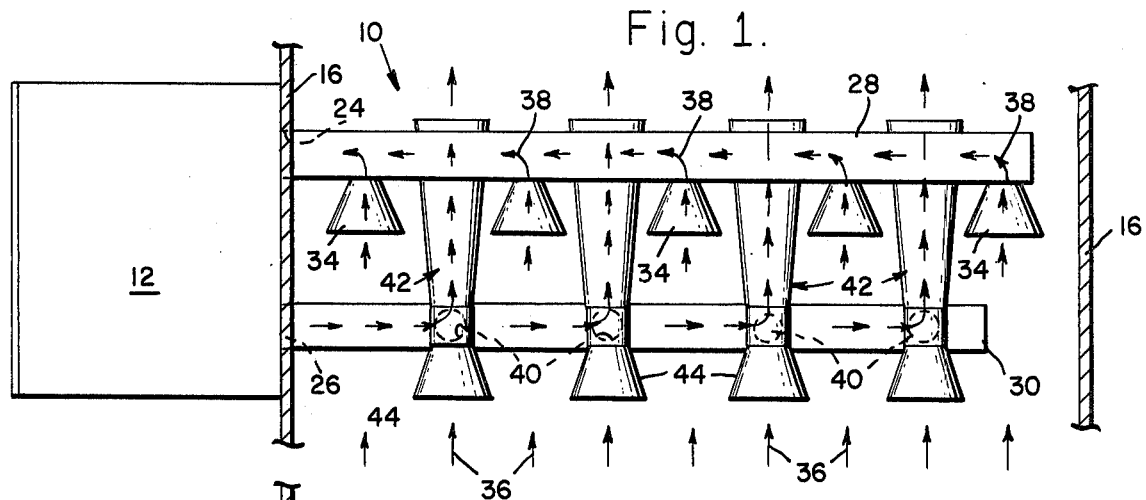
FIG. 1 is a top view of the invention shown in position within an air duct.
Figure 2:
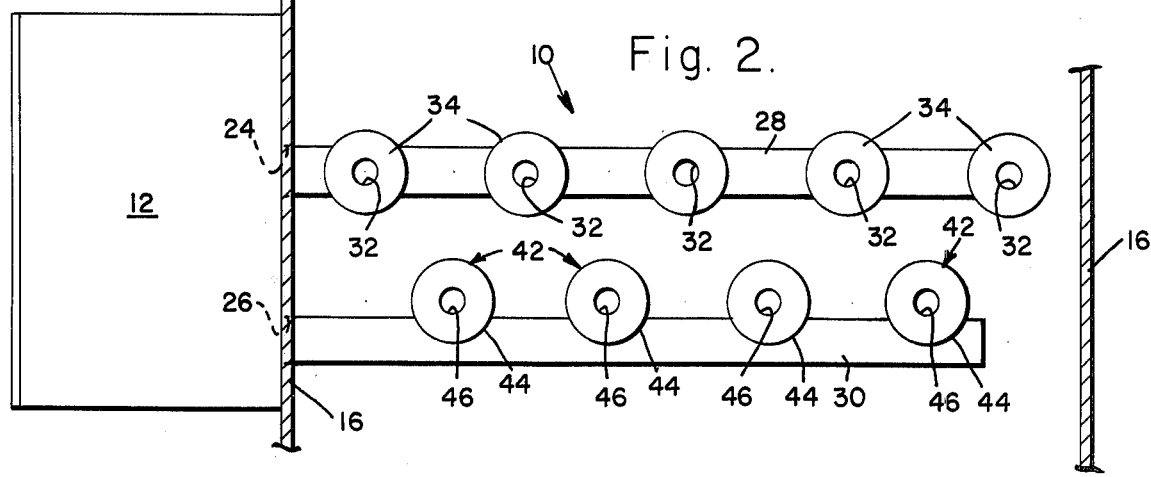
FIG. 2 is a front view of the invention taken at right angles with respect to the top view illustrated in FIG. 1.
Figure 3:
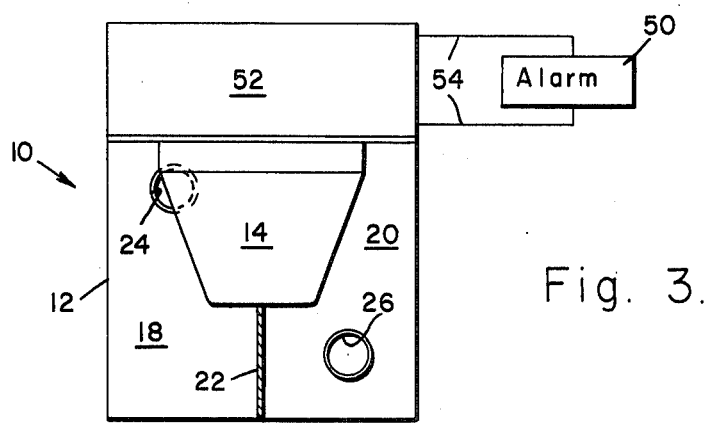
FIG. 3 is a view of the detector showing an inlet to and an outlet from the duct shown in FIGS. 1 and 2.

Referring to FIGS. 1 through 3, a fluid sampler 10 is configured specifically for illustrative purposes as an air sampler. It comprises an enclosure 12 for housing a detector 14, which is of any conventional design. For use in detecting products of combustion in a vapor state, particulate matter, and smoke, the basic types of detector include an ionization detector and a photocell detector. However, when it is desired to measure the content of other fluids or gases, the particular detector used will be conformed thereto. Such a detector 10 is secured to a duct or similar means through which fluid flows, as defined by walls 16.

As shown in FIG. 3, enclosure 12 is separated into two portions 18 and 20 by a divider plate 22 and detector 14. An opening 24 forms the inlet to chamber 18 while an opening 26 forms the outlet from chamber 20. Flow of fluid from chamber 18 to chamber 20, therefore, must be through detector 14. Secured respectively to openings 24 and 26 are an impact tube 28 and an outlet tube 30. Disposed along the length of impact tube 28 are a plurality of openings 32 and secured to tube 28 at openings 32 are cones 34. As shown in FIG. 1, openings 32 and cones 34 face into the direction of fluid flow, as depicted by arrows 36. Therefore, fluid flowing towards cones 34 impacts and enters into chamber 18 of enclosure 10 as shown by arrows 38.

Provided in outlet tube 30 also are a plurality of openings 40 and secured to tube 30 at the openings respectively are venturi tubes 42. As is known, a venturi tube has an opening 44 which decreases in cross section to a throat 46 which then expands to an outlet at 48. In the present invention, each venturi tube 42 has an opening in its neck 46 which is secured to its respective hole 40 in outlet tube 30 to provide for fluid communication between tubes 30 and 42. Mouths 44 of venturi tubes 42 also face into the direction of flow 36 of the fluid.

In operation, air or other fluid passing through duct 16 is drawn into impact tube 28 through openings 32 as aided by cones 34. Similar air passing through venturi tubes 42 creates a pressure therein at throat 46 which is negative with respect to impact tube 28. This negative pressure creates an increased pressure differential which actively aides in drawing air into impact tube 28 and thence throgh detector 14. As a consequence, not only is a sampling of the air flowing through a duct insured but also the quantity of the sample is greatly increased. When the sampling of the air is for smoke detection, an alarm 50 may be electrically coupled to detector 14 by conventional electronic circuitry 52 and wiring 54.

It is preferred that entrance cones 34 be placed in a manner so that they extend completely across the duct between walls 16 so as to obtain a representative, cross-sectional sample of the fluid. The venturi tubes are preferably placed at the center of the duct where the greatest amont of air flows. Any number of venturies may be utilized and, as the number of venturi tubes increase, the air sample also increases.

Figure 4A:
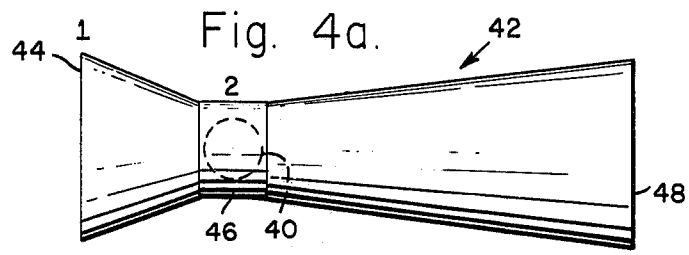
FIGS. 4a and 4b are views of two elements of the invention for use as an aid in describing the operation thereof.
Figure 4B:
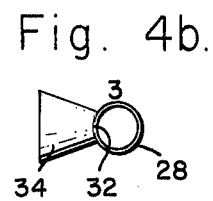

For a greater understanding of the present invention, reference to FIGS. 4a and 4b is made. FIG. 4a depicts a single venturi tube 42 while FIG. 4b depicts impact tube 28 and one of its openings 32 at cones 34. Reference numeral 1 is placed at mouth 44 or opening of venturi tube 42 and reference numeral 2 is placed at its throat 46. A reference numeral 3 is used at opening 32 of impact tube 28. While the following discussion of fluid dynamics and the formulas therefor are directed specifically for air, comparable analysis is the same for other fluid systems. For air, the relationship between the velocity of air measured, for example, in feet per minute is related to the velocity head of the air, measured in inches of water according to the formula:

$$V = 4008(h_V)^{\frac{1}{2}} \quad (1)$$

where V is the velocity of the air, $h_V$ is the velocity head or pressure difference (inches of water). The pressures associated with the given volume of fluid, for example, flowing through walls 16 in FIGS. 1 and 2, is directly proportional to the energy content of that fluid in that the total pressure is equal to the velocity pressure plus the static pressure. This relationship at points 1, 2 and 3 of FIGS. 4a and 4b is given by the following expression:

$$h_{TP1} = h_{TP2} = h_{TP3} = h_{V1} + h_{SP1} = h_{V2} + h_{SP2} = h_{V3} + h_{SP3} \quad (2)$$

where $h_{TP}$ is the total pressure, $h_V$ is the velocity head, and $h_{SP}$ is the static pressure, all in inches of water, at their respective points 1, 2 and 3. This formula is true where impact tube 28 and exit tube 30 are closely placed to one another or where the air velocity is the same for both tubes 28 and 30.

Assuming a static pressure of three quarter inches of water, which is reasonable for conventional air conditioning systems, at a flow velocity (V) of 300 feet per minute at point 1, that is, at mouth 44, from formula (1) the velocity head ($h_{V1}$) is 0.0056 inches of water. Because total pressure always equals velocity pressure plus static pressure, for a static pressure of three quarter inches of water or 0.75, the total pressure at point 1 ($h_{TP1}$) is 0.7556 inches of water (0.75 + 0.0056). Assuming a throat 46 which is one half the area of mouth 44, the velocity of air would therefore double from that at mouth 44 or a velocity (V) of 600 feet per minute. From formula (1) a velocity (V) of 600 feet per minute provides a velocity head ($h_{V2}$) of 0.224 inches of water. Because the total pressure is constant in the system, that is, 0.7556 inches of water as previously determined in this example, to obtain the static pressure ($h_{SP2}$), the velocity head ($h_{V2}$) is subtracted from the total pressure ($h_{TP2}$) to obtain the static pressure at poit 2 ($h_{SP2}$) = 0.7332.

At point 3, that is at impact tube 28, as the flow of air into impact tube 28 approaches zero velocity ($h_{V3} \rightarrow 0$), its static pressure ($h_{SP3}$) approaches that of the total pressure ($h_{TP3}$). Therefore, the static pressure at point 3 ($h_{SP3}$) is approximately equal to the total pressure at point 3 ($h_{TP3}$), or 0.7556 inches of water. To find the pressure differential, the static pressure ($h_{SP2}$) at point 2 is subtracted from the total pressure ($h_{TP3}$) at point 3, or 0.0224 inches of water for the example given.

For a conventional system as described above, for a flow of 300 feet per minute, the pressure differential is 0.0056 inches of water. As compared to the present invention's pressure differential of 0.0224 inches of water, the difference (0.0168 inches of water) is approximately for times. Measurements of fluid flows extending from 150 feet per minute to 4,000 feet per minute also provided an approximate four times increase in the amount of fluid drawn into the detector such as detector 14 over conventional systems. The result is a greater sensitivity obtainable by means of the invention as well as a greater ability for sufficient contaminants or other sample material to be delivered to the detector in order to reach its threshold. Thus, it is possible, as verified by experiment, to accurately sample air flows of 100 feet per minute while prior art systems have not been able to measure samples under 500 feet per minute. Also because of the larger sampling capabilities of the present invention, a faster response with respect to the prior art results because the invention provides for a greater pressure differential for a given velocity.

Although the invention has been described with reference to a particular embodiment thereof, it should be realized that various changes and modifications may be made therein without departing from the spirit and scope of the invention.

What is claimed is:

1. A fluid sampling system comprising means defining the path of flow of a fluid, a detector having an inlet and an outlet respectively for enabling said detector to sample said fluid, an impact tube having a plurality of openings coupled between said flow path means and said detector inlet and spaced across substantially the flow path for collecting representative cross-sectional samples of said fluid for supply thereof to said detector, another tube coupled to and extending from said detector outlet, a plurality of venturi tubes in said flow path means and secured to said another tube for creating a fluid pressure in said detector which is negative with respect to said detector inlet, said openings and said venturi tubes both facing into the direction of the flow of said fluid.

2. A fluid sampling system as in claim 1 wherein said detector is positioned exterior to said flow path means.

3. A fluid sampling system as in claim 1 wherein said flow path means comprises an air duct.

4. A fluid sampling system as in claim 1 wherein said detector comprises a smoke detector for detecting products of combustion.

5. A fluid sampling system as in claim 1 further including funnels secured to said openings for directing said fluid into said openings.

* * * * *